United States Patent
Kadreppa et al.

(10) Patent No.: US 10,590,455 B2
(45) Date of Patent: Mar. 17, 2020

(54) PROCESS FOR MODIFYING GALACTOSYLATION AND G₀F CONTENT OF A GLYCOPROTEIN COMPOSITION BY GLUTAMINE SUPPLEMENTATION

(71) Applicant: DR. REDDY'S LABORATORIES LIMITED, Hyderabad (IN)

(72) Inventors: Sreenath Kadreppa, Hyderabad (IN); Madhava Ram Paranandi Ananta, Hyderabad (IN); Senthil Kumar Baskaran, Madurai (IN); Shinto Antony, Haridwar (IN)

(73) Assignee: DR. REDDY'S LABORATORIES LIMITED, Hyderabad (IN)

( * ) Notice: Subject to any disclaimer, the term of this patent is extended or adjusted under 35 U.S.C. 154(b) by 389 days.

(21) Appl. No.: 15/121,361

(22) PCT Filed: Feb. 24, 2015

(86) PCT No.: PCT/IB2015/051367
§ 371 (c)(1),
(2) Date: Aug. 24, 2016

(87) PCT Pub. No.: WO2015/128795
PCT Pub. Date: Sep. 3, 2015

(65) Prior Publication Data
US 2016/0362714 A1  Dec. 15, 2016

(30) Foreign Application Priority Data
Feb. 25, 2014 (IN) .............................. 928/CHE/2014

(51) Int. Cl.
*C12P 21/00* (2006.01)
*C07K 16/22* (2006.01)

(52) U.S. Cl.
CPC ............ *C12P 21/005* (2013.01); *C07K 16/22* (2013.01); *C07K 2317/14* (2013.01); *C07K 2317/41* (2013.01); *C07K 2317/732* (2013.01); *C07K 2317/734* (2013.01)

(58) Field of Classification Search
None
See application file for complete search history.

(56) References Cited

U.S. PATENT DOCUMENTS

| | | |
|---|---|---|
| 7,060,269 B1 | 6/2006 | Baca et al. |
| 2008/0081356 A1 | 4/2008 | Lasko et al. |
| 2011/0136682 A1 | 6/2011 | Bosques et al. |
| 2012/0276631 A1 | 11/2012 | Bengea et al. |
| 2015/0344579 A1 | 12/2015 | Thuduppathy et al. |

FOREIGN PATENT DOCUMENTS

| | | | |
|---|---|---|---|
| WO | 02/101019 A2 | 12/2002 | |
| WO | WO 2008/008360 | * 1/2008 | ............... C12N 5/00 |
| WO | 2013/114165 A1 | 8/2013 | |
| WO | 2013/114167 A1 | 8/2013 | |

OTHER PUBLICATIONS

Extended European Search Report mailed by the European Patent Office dated Sep. 18, 2017, for corresponding European Patent Application No. EP 15 75 5326.

Tang et al., "Pharmacokinetic Aspects of Biotechnology Products", Journal of Pharmaceutical Sciences, Sep. 2004, pp. 2184 to 2204, vol. 93—issue No. 9, Wiley-Liss, Inc. and the American Pharmacists Association.

Andersen et al. , "Multiple Cell Culture Factors Can Affect the Glycosylation of Asn-184 in CHO-Produced Tissue-Type Plasminogen Activator", Biotechnology and Bioengineering, Oct. 5, 2000, pp. 25 to 31, vol. 70—issue No. 1, John Wiley & Sons, Inc.

Michael Butler, "Animal cell cultures: recent achievements and perspectives in the production of biopharmaceuticals", Appl Microbiol Biotechnol, 2005, pp. 283 to 291, vol. 68, Springer-Verlag.

Yamane-Ohnuki et al., "Establishment of FUT8 Knockout Chinese Hamster Ovary Cells: An Ideal Host Cell Line for Producing Completely Defucosylated Antibodies With Enhanced Antibody-Dependent Cellular Cytotoxicity", Biotechnology and Bioengineering, Sep. 5, 2004, pp. 614 to 622, vol. 87—issue No. 5, Wiley Periodicals, Inc.

Mori et al., "Engineering Chinese Hamster Ovary Cells to Maximize Effector Function of Produced Antibodies Using FUT8 siRNA", Biotechnology and Bioengineering, Dec. 30, 2004, pp. 901 to 908, vol. 88—issue No. 7, Wiley Periodicals, Inc.

Ferrara et al., "Modulation of Therapeutic Antibody Effector Functions by Glycosylation Engineering: Influence of Golgi Enzyme Localization Domain and Co-Expression of Heterologous β1, 4-N-acetylglucosaminyltransferase III and Golgi α-mannosidase II", Biotechnology and Bioengineering, Apr. 5, 2006, pp. 851 to 861, vol. 93—issue No. 5, Wiley Periodicals, Inc.

Yazawa et al., "α-L-Fucosidase From Aspergillus Niger: Demonstration of a Novel α-L-(1 → 6)-Fucosidase Acting on Glycopeptides", Biochemical and Biophysical Research Communications, Apr. 29, 1986, pp. 563 to 569, vol. 136—issue No. 2, Academic Press, Inc.

Yamamoto et al., "Chemical Synthesis of a Glycoprotein Having an Intact Human Complex-Type Sialyloligosaccharide under the Boc and Fmoc Synthetic Strategies", J. Am. Chem. Soc., 2008, pp. 501 to 510, vol. 130—issue No. 2, American Chemical Society.

Konno et al., "Controlling Fucosylation Levels of Antibodies with Osmolality during Cell Culture", Animal Cell Technology: Basic & Applied Aspects, pp. 121 to 125, vol. 16, Springer Science+Business Media B.V.

(Continued)

*Primary Examiner* — Suzanne M Noakes
*Assistant Examiner* — Jae W Lee
(74) *Attorney, Agent, or Firm* — Pergament & Cepeda LLP; Milagros A. Cepeda; Edward D. Pergament

(57) ABSTRACT

The invention relates to a cell culture process for decreasing the galactosylated content and/or increasing the G0F content of a glycoprotein. The process involves subjecting recombinant cells expressing the said glycoprotein to a temperature and pH shift and supplementing cell culture with glutamine.

15 Claims, 4 Drawing Sheets

(56) References Cited

OTHER PUBLICATIONS

Hodoniczky et al., "Control of Recombinant Monoclonal Antibody Effector Functions by Fc N-Glycan Remodeling in Vitro", Biotechnol. Prog., 2005, pp. 1644 to 1652, vol. 21—issue No. 6, American Chemical Society and American Institute of Chemical Engineers.

Marino et al., "A systematic approach to protein glycosylation analysis: a path through the maze", Nature Chemical Biology, Oct. 2010, pp. 713 to 723, vol. 6, Nature America, Inc.

Wuhrer et al., "Protein glycosylation analysis by liquid chromatography-mass spectrometry", Journal of Chromatography B, 2005, pp. 124 to 133, vol. 825, Elsevier B.V.

Guile et al., "A Rapid High-Resolution High-Performance Liquid Chromatographic Method for Separating Glycan Mixtures and Analyzing Oligosaccharide Profiles", Analytical Biochemistry, 1996, pp. 210 to 226, vol. 240, Academic Press, Inc.

International Search Report dated May 29, 2015, for corresponding International Patent Application No. PCT/IB2015/051367.

Written Opinion dated May 29, 2015, for corresponding International Patent Application No. PCT/IB2015/051367.

International Preliminary Report on Patentability dated Aug. 30, 2016, for corresponding International Patent Application No. PCT/IB2015/051367.

Zhong and Somers, "Recent Advances in Glycosylation Modifications in the Context of Therapeutic Glycoproteins", Integrative Proteomics, Feb. 24, 2012, pp. 183 to 196, InTech.

Shinkawa et al., "The Absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity", The Journal of Biological Chemistry, Nov. 8, 2002, pp. 3466 to 3473, vol. 278—issue No. 5, The American Society for Biochemistry and Molecular Biology, Inc.

T. Shantha Raju, "Glycosylation Variations with Expression Systems and Their Impact on Biological Activity of Therapeutic Immunoglobulins", BioProcess International, Apr. 2003, pp. 44 to 53.

Peipp et al., "Antibody fucosylation differentially impacts cytotoxicity mediated by NK and PMN effector cells", Immunobiology, Blood, Sep. 15, 2008, pp. 2390 to 2399, vol. 112—issue No. 6, The American Society of Hematology.

Ruhaak et al., "Glycan labeling strategies and their use in identification and quantification", Anal Bioanal Chem, 2010, pp. 3457 to 3481, vol. 397, Springer.

* cited by examiner

PROCESS FOR MODIFYING GALACTOSYLATION AND G$_0$F CONTENT OF A GLYCOPROTEIN COMPOSITION BY GLUTAMINE SUPPLEMENTATION

This application is a National Stage Application under 35 U.S.C. § 371 of PCT International Application No. PCT/IB2015/051367, filed Feb. 24, 2015, which claims the benefit of Indian Provisional Application 928/CHE/2014, filed Feb. 25, 2014, all of which are hereby incorporated by references in their entireties.

INTRODUCTION

The invention describes a method for obtaining a glycoprotein with a particular glycoform composition. Particularly, the invention relates to a cell culture process for reducing the galactosylation content and/or increasing the G$_0$F content of a glycoprotein by supplementing cell culture medium with glutamine.

Protein glycosylation is one of the most important post-translation modifications associated with eukaryotic proteins. This is evidenced by the fact that more than 50% of the eukaryotic proteins are glycosylated (Apweiler et al., 1999, Biochim Biophys Acta 1473(1):4-8.). The structure and composition of the saccharide (glycan) moieties added can have profound effect on the stability, safety and efficacy of these proteins (Wong C H, 2005, J Org Chem 70(11):4219-25). Hence, an understanding of glycosylation and modes of controlling the same are of immense significance.

Broadly, the two major types of glycosylation in eukaryotic cells are —N-linked glycosylation in which glycans are attached to the asparagine residue and O-linked glycosylation in which glycans are attached to serine or threonine residues. Further, N-linked glycans are of two types—'high mannose' glycans consisting of two N-acetylglucosamines plus a large number of mannose residues (more than 4), and 'complex' glycans that contain more than two N-acetylglucosamines plus any number of other types of sugars. In both N- and O-glycosylation, there are usually a range of glycan structures associated with each site.

Among glycoproteins, monoclonal antibodies (mAbs) have emerged as major therapeutic agents against various conditions (Thong X. and Somers W., 2012, Recent Advances in Glycosylation Modifications in the Context of Therapeutic Glycoproteins, Integrative Proteomics, ISBN: 978-953-51-0070-6). The in-vivo physiological activity of mAbs is mediated by two independent mechanisms, (a) target antigen neutralization or apoptosis and (b) antibody effector functions which include antibody-dependent cellular cytotoxicity (ADCC) and complement-dependent cytotoxicity (CDC). Importantly, the effector functions of antibodies has been shown to correlate with the glycan structures associated with these mAbs. Further, glycosylation of mAbs are also known to improve therapeutic efficacy through its impact on protein pharmacodynamics (PD) and pharmacokinetics (PK) (Mahmood I, Green M D, 2005, Clin Pharmacokinet 44(4):331-47; Tang et al., 2004, J Pharm Sci 93(9):2184-204.). The N-glycosylation in mAbs involves attachment of oligosaccharides at asparagine (Asn)-297 in the CH$_2$ domain of Fc region of IgGs. This is a unique feature of IgG, making it a "key player" in functioning of the immune system. However, mAb homogeneity is difficult to achieve, complicated by the fact that recombinant systems, used for the large scale production of these therapeutic antibodies may secrete IgGs with altered and significant variation in the glycan structures. This can potentially result in suboptimal effector functions of these antibodies. Clearly, methods for improving, controlling and modifying glycosylation have immense impact on the production and functionality of therapeutic mAbs.

Several factors affect glycosylation profile of a glycoprotein. These include cell line characteristics, process control parameters and cell culture media components (Andersen et al., 2000, Biotechnol Bioeng 70(1):25-31.; Butler, 2005, Appl Microbiol Biotechnol. 68(3):283-291.) A number of strategies exist in the prior art to modulate compositions of different glycoforms in an antibody composition. One of the suggested approaches is genetic manipulation of the cell lines for glycosyl transferases, enzymes responsible for glycosylation (Yamane-Ohnuki et al., 2004, Biotechnol Bioeng., 87:614-622; Shinkawa et al., 2003, J. Biol. Chem., 278:3466-73; Mori et al., 2004, Biotechnol Bioeng., 88:901-8; Ferrara et al., 2006, Biotechnol Bioeng., 93:851-61).

Other methods include in vitro modification of proteins post protein synthesis to obtain desired glycoprotein (Inazu T., 2007, Research in construction of the complex system for functional oligosaccharides. Proceeding of the Institute of Glycotechnology of Tokai University; 2:42-45; Yazawa et al., 1986, Biochem Biophys Res Commun. 1986; 136:563-569; Yamamoto et al., 2008, J. Am. Chem. Soc., 130:501-10). Modifications in cell culture conditions and media compositions have also been proposed to modulate glycosylation content of glycoproteins. For example, it has been demonstrated that, for the mAbs produced in the rat hybridoma cell line YB2/0 there is a direct correlation between osmolality of the culture medium and afucosylation (Yoshinobu et al., 2010, Animal Cell Technology: Basic & Applied Aspects Volume 16, pp 121-125). Makkapati et al. have described a cell culture process for obtaining a glycoprotein composition comprising about 14% to about 18% total afucosylated glycans by culturing cells in a medium supplemented with galactose, at a specific osmolality, and harvesting on about 12th day or at about 50% viability (WO2013114165 A1). Ramasamy et al. have demonstrated the role of manganese in increasing Mans glycans and/or afucosylated glycans in a glycoprotein composition (WO2013114245 A1). Further, US 2012/0276631 A1 teaches about the use of Mn ion and/or D-galactose in the culture media to modulate galactosylation.

Effect of Galactosylation and Fucosylation on mAbs

Several studies have suggested that the terminal galactose content of IgG improves CDC as a result of increased antibody binding to C1q, without impacting the ADCC activity (Hodoniczky J, Zheng Y Z, James D C: Control of recombinant monoclonal antibody effector functions by Fc N-glycan remodeling in vitro. Biotechnol Prog 2005, 21:1644-1652). Further, addition of galactose is a template for addition of sialic acid on mAbs (Mariño, K., (2010) Nature Chemical Biology 6,713-723). This increased terminal sialylation can increase the serum half-life of many glycoproteins (Raju T S: Glycosylation variations with expression systems and their impact on biological activity of therapeutic immunoglobulins. Bioprocess Int 2003, 1:44-53). However, in contrast, studies have also demonstrated that increased sialylation of Fc glycans results in decreased ADCC activity of rIgGs. (Scallon B J, Tam S H, McCarthy S G, Cai A N, Raju T S: Higher levels of sialylated Fc glycans in immunoglobulin G molecules can adversely impact functionality. Mol Immunol 2007, 44:1524-1534). Without being bound by theory a decreased galactosylation will result in a decreased sialylation and hence may prevent the decrease in ADCC activity of rIgGs. Additionally, it has been demonstrated that the absence of core fucose residues in the Fc glycans substantially increases the ADCC activity of IgG as nonfucosylated antibodies bind to the FcgRIIIa receptor with significantly increased affinity. However in contrast, Peipp M. et al have shown that polymorphonuclear cells preferentially kill via high-fucosylated antibody composition. Further, high-fucose antibody induced superior ADCC in blood from granulocyte colony-stimulating factor-primed donors containing higher numbers of activated polymorphonuclear cells. Since, the impact of fucosylation on ADCC activity is primarily dependent on the effector cells employed, it may be desirable to obtain an antibody composition comprising decreased afucosylated content (Peipp M, Blood. 2008 Sep. 15; 112(6):2390-9. doi: 10.1182/blood-2008-03-144600).

Thus, considering the positive effect of agalactosylation and fucosylation on the use of monoclonal antibodies as therapeutics, the present invention discloses a cell culture process which produces an antibody composition comprising increased percentage of $G_0F$ glycoform.

The present invention explores the role of an essential amino acid, L-glutamine in modifying the glycan composition of a glycoprotein. Glutamine as a supplement or as a cell culture medium component has been in use for increasing cell viability or product titer. However, the effect of glutamine on glycosylation of proteins is not known. The present invention provides a cell culture process for obtaining a glycoprotein composition with reduced galactosylation and/or increased $G_0F$ glycans.

SUMMARY

The present invention describes a cell culture process for modifying galactosylation and/or $G_0F$ in a glycoprotein composition by culturing the recombinant cells producing said glycoprotein in a medium supplemented by glutamine.

In addition, the present invention is advantageous in that the modulation of glycoform composition by varying concentration of glutamine does not affect the titer of the culture. In other words, the invention allows the flexibility of choosing a concentration of glutamine to be used in cell culture, depending upon the glycoform composition required, without compromising on titer.

DETAILED DESCRIPTION OF THE INVENTION

Definitions

Figure 1:
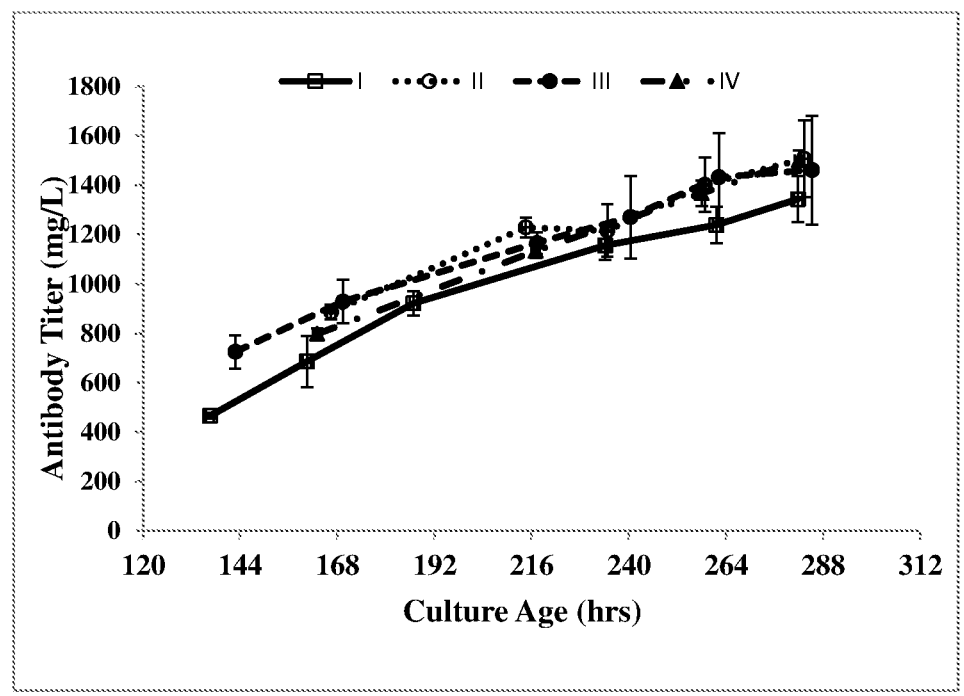
FIG. 1 is an illustration of antibody titer as described in Examples I and II.

The term "glycan" refers to a monosaccharide or polysaccharide moiety.

The term "glycoprotein" refers to protein or polypeptide having at least one glycan moiety. Thus, any polypeptide attached to a saccharide moiety is termed as glycoprotein.

The term "glycoform" or "glycovariant" have been used interchangeably herein, and refers to various oligosaccharide entities or moieties linked in their entirety to the Asparagine 297 (as per Kabat numbering) of the human Fc region of the glycoprotein in question, co translationally or post translationally within a host cell. The glycan moieties may be added during protein glycosylation include $M_3$, $M_4$, $M_{5-8}$, $M_3NAG$ etc. Examples of such glycans and their structures are listed in Table 1. However, Table 1 may not be considered to limit the scope of this invention to these glycans.

The "glycoform composition" or distribution as used herein pertains to the quantity or percentage of different glycoforms present in a glycoprotein.

As used herein, "high mannose glycovariant" consists of glycan moieties comprising two N-acetylglucosamines and more than 4 mannose residues i.e. $M_5$, $M_6$, $M_7$, and $M_8$.

"Galactosylated glycans" refers to glycans containing terminal galactose residues such as $G_{1A}$, $G_{1B}$, $G_{1A}F$, $G_{1B}F$, $G_2$, $G_2F$ and $G_2SF$.

$G_0$ as used herein refers to protein glycan not containing galactose at the terminal end of the glycan chain.

$G_0F$ as described here consists of glycan moieties wherein fucose is linked to the non-reducing end of N-acetylglucosamine.

Various methods described in the art such as Wuhrer et. al., Ruhaak L. R., and Geoffrey et. al. can be used for assessing glycovariants present in a glycoprotein composition (Wuhrer M. et al., Journal of Chromatography B, 2005, Vol. 825, Issue 2, pages 124-133, Ruhaak L. R., Anal Bioanal Chem, 2010, Vol. 397:3457-3481, Geoffrey, R. G. et. al. Analytical Biochemistry 1996, Vol. 240, pages 210-226).

The term "temperature shift" as used herein is defined as the change in temperature during the cell culture process.

The term "pH shift" as used herein is defined as the change in pH during the cell culture process.

As used herein, "IVCC" or "Integral viable cell concentration" refers to cell growth over time or integral of viable cells with respect to culture time that is used for calibration of specific protein production. The integral of viable cell concentration can be increased either by increasing the viable cell concentration or by lengthening the process time.

TABLE I

Representative table of various glycans

| Glycan structure | Code |
|---|---|
|  | $M_3$ |
|  | $M_6$ |

TABLE I-continued

Representative table of various glycans

| Glycan structure | Code |
|---|---|
| | $M_3NAG$ |
| | $G_2F$ |
| | $M_3NAGF$ |
| | $M_7$ |
| | $G_0$ |
| | $G_2SF$ |
| | $G_0F$ |￼

TABLE I-continued

Representative table of various glycans

| Glycan structure | Code |
|---|---|
| | $M_8$ |
| | $M_5$ |
| | $G_2S_2F$ |
| | $G_{1A}$ |
| | $G_{1A}F$ |
| | $G_{1B}$ |

TABLE I-continued

Representative table of various glycans

| Glycan structure | Code |
|---|---|
| | $G_{1B}F$ |

Mannose ◆

N-Acetyl Glucosamine ●

Galactose ■

2-AB Label ✛

Fucose ☐

Sialic acid ▷

DETAILED DESCRIPTION OF THE EMBODIMENTS

The present invention discloses a cell culture process for production of a glycoprotein composition containing increased percentage of $G_0F$ glycans and/or reduced percentage of galactosylated glycans.

In an embodiment, the present invention provides a cell culture process for obtaining a glycoprotein composition with increased percentage of $G_0F$ glycans and/or reduced percentage of galactosylated glycans comprising
 a) culturing cells at a first temperature and a first pH for a first period of time
 b) culturing cells at a second temperature and a second pH for a second period of time
 c) supplementing said cell culture with L-glutamine
 d) recovering protein from the cell culture.

In another embodiment, the present invention provides a process for obtaining a glycoprotein composition comprising about 16% to about 25% galactosylated glycans.

In yet another embodiment, the present invention provides a process for obtaining a glycoprotein composition comprising about 66% to about 74% of $G_0F$ glycans.

In a further embodiment, the present invention provides a process for obtaining a glycoprotein composition comprising about 66% to about 74% of $G_0F$ glycans and about 16% to about 25% galactosylated glycans.

In another embodiment, the present invention provides a method for obtaining glycoprotein composition wherein the galactosylated glycan percentage is decreased by about 27% to about 46%.

In yet another embodiment, the present invention provides a method for obtaining glycoprotein composition wherein the percentage of $G_0F$ glycans is increased by about 13% to about 21% as compared to the control.

In another embodiment the cell culture medium is supplemented with about 4 mM of glutamine.

In yet another embodiment the cell culture medium is supplemented with about 8 mM of glutamine.

In a further embodiment the cell culture medium is supplemented with about 12 mM of glutamine.

In another embodiment, the invention provides a method for production of glycoproteins with increased percentage of $G_0F$ glycans and/or reduced percentage of galactosylated glycans wherein the cells are subjected to temperature shift(s). The temperature shift may be a temperature upshift wherein the later temperature is at a higher value than the earlier value or a temperature downshift wherein the later temperature is at a lower value than the earlier value.

In yet another embodiment, the invention provides a method for production of glycoproteins with a particular glycoform composition by first culturing cells at temperature of about 35° C.-about 37° C., followed by lowering of temperature by about 2° C.-about 7° C.

In a further embodiment, the invention provides a method for expression of protein with particular glycoform composition by growing cells at about 37° C., followed by subjecting cells to about 35° C.

In another embodiment, the invention provides method for production of glycoproteins with increased percentage of $G_0F$ glycans and/or reduced percentage of galactosylated glycans wherein the cells are subjected to pH shift(s). The pH shift may be a pH upshift wherein the later pH is at a higher value than the earlier value or a pH downshift wherein the later pH is at a lower value than the earlier value.

In yet another embodiment, the invention provides method for production of glycoproteins with a particular glycoform composition by first culturing cells at a pH of about 7.1 followed by culturing cells at a pH reduced by about 0.1 unit to about 0.5 unit.

In a further embodiment, the invention provides method for production of glycoproteins with a particular glycoform composition by first culturing cells at a pH of about 7.1 followed by culturing cells at a pH of about 6.9.

In another embodiment the shift in temperature and pH may be accompanied by addition of nutrient feed.

In any of the embodiments mentioned above, titer of the culture is not altered or decreased.

The cell culture media that are useful in the invention include but are not limited to, the commercially available products PF-CHO (HyClone), PowerCHO®2 (Lonza), Zap-CHO (Invitria), CD CHO, CD OptiCHO™ and CHO-S-SFMII (Invitrogen), ProCHO™ (Lonza), CDM4CHO™ (Hyclone), DMEM (Invitrogen), DMEM/F12 (Invitrogen), Ham's F10 (Sigma), Minimal Essential Media (Sigma), and RPMI-1640 (Sigma) or combinations thereof. Further, the cell culture medium can be a combination of any aforementioned cell culture medium and a feed.

The cell culture feed that are useful in the invention include but are not limited to, the commercially available products Cell Boost 2 (CB-2, Thermo Scientific Hyclone, Catalogue no SH 30596.03), Cell Boost 4 (CB-4, Thermo Scientific HyClone, Catalog no. SH30928), PF CHO (Thermo Scientific Hyclone, Catalog no. SH30333.3).

The feed or feed medium in the present invention may be added in a continuous, profile or a bolus mode. One or more feeds may be added in one manner (e.g. profile mode), and other feeds in second manner (e.g. bolus or continuous mode). Further, the feed may be composed of nutrients or other medium components that have been depleted or metabolized by the cells. The feed may be concentrated form of initial cell culture media itself or may be a different culture media. The components may include hormones, growth factors, ions, vitamins, nucleoside, nucleotides, trace elements, amino acids, lipids or glucose. Supplementary components may be added at one time or in series of additions to replenish depleted nutrients. Thus the feed can be a solution of depleted nutrient(s), mixture of nutrient(s) or a mixture of cell culture medium/feed providing such nutrient(s).

Certain aspects and embodiments of the invention are more fully defined by reference to the following examples. These examples should not, however, be construed as limiting the scope of the invention.

EXAMPLES

Example I

Figure 2:
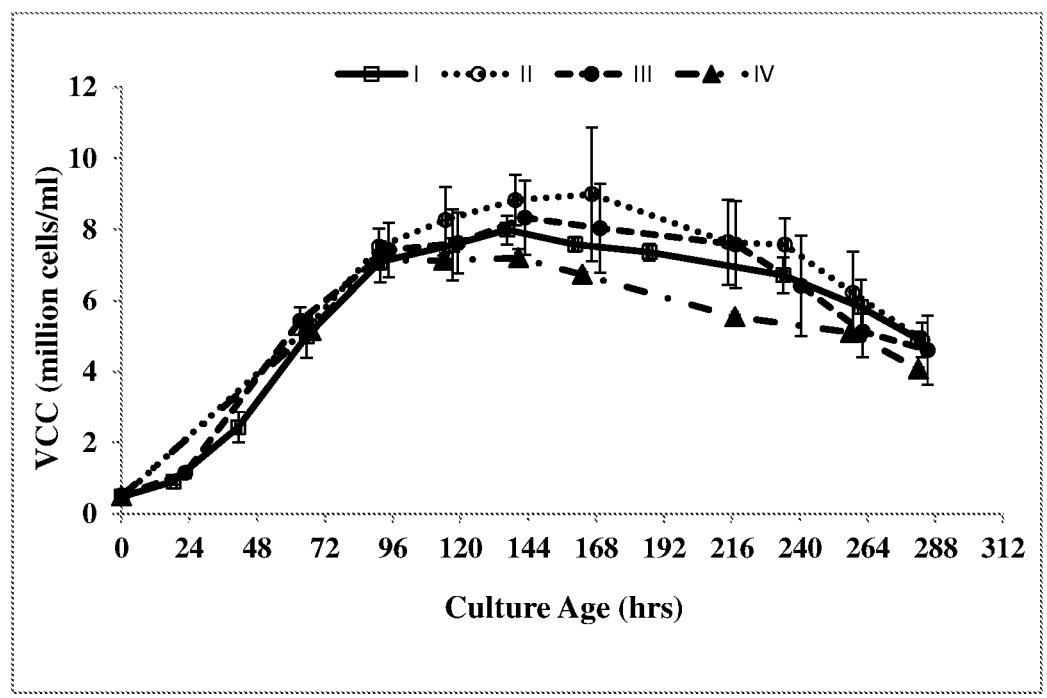
FIG. 2 is an illustration of viable cell count as described in Examples I and II.
Figure 3:
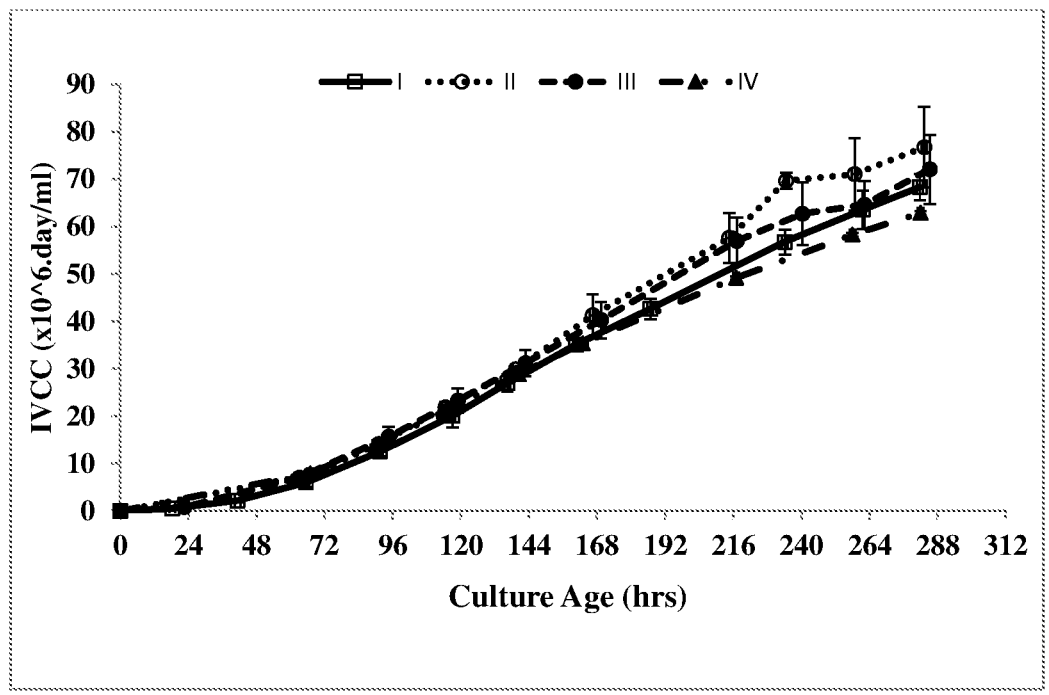
FIG. 3 is an illustration of IVCC as described in Examples I and II.
Figure 4:
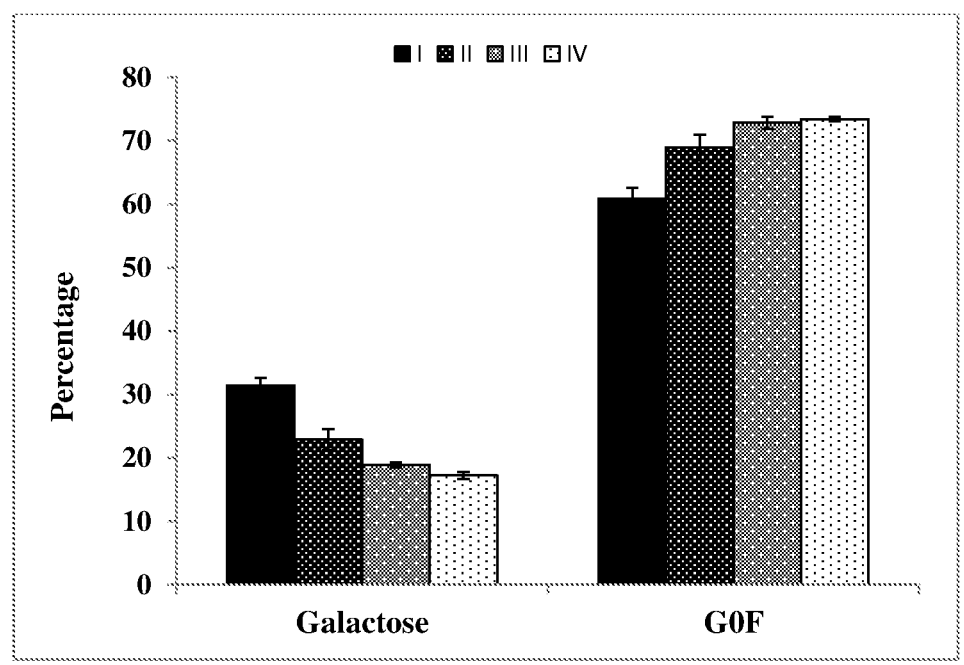
FIG. 4 is an illustration of percentage of $G_0F$ and galacotsylated glycans as described in Examples I and II.

An anti-VEGF antibody was cloned and expressed in a recombinant CHO cell line as described in U.S. Pat. No. 7,060,269, which is incorporated herein by reference. rCHO cells expressing antibody at a seeding density of 0.2-0.6 million cells/ml were seeded in cell culture media (Power-CHO®2 (Lonza, Catalog no: 12-771Q) and CB4 feed, 95:5) at 37° C. and pH 7.1. The cells were cultured for 64 hours (2-3 days after inoculation of culture), subsequently pH was reduced to 6.9 and temperature was reduced to 35° C. followed by addition of the feed CB-4. The culture was finally harvested after 240 hrs to 288 hrs or at greater than 50% viability. The experiment was run in thirteen separate batches and the average values (I) for antibody titer, VCC, IVCC and percentage of $G_0F$ and galactosylated glycans are shown in FIG. 1-4. The percentage of $G_0F$ glycan and galactosylated glycan values are depicted in Table II.

Example II

An anti-VEGF antibody was cloned and expressed in a recombinant CHO cell line as described in U.S. Pat. No. 7,060,269, which is incorporated herein by reference. rCHO cells expressing antibody at a seeding density of 0.2-0.6 million cells/ml were seeded in cell culture media (Power-CHO®2 (Lonza, Catalog no: 12-771Q) and CB-4 feed, 95:5) at 37° C. and pH 7.1. The cells were cultured for 64 hours (2-3 days after inoculation of culture), subsequently pH was reduced to 6.9 and temperature was reduced to 35° C. followed by addition of the feed CB-4. On day 4 after seeding (inoculation of the culture), 4 mM (II of Table II) of L-glutamine was added to the cell culture medium. The culture was finally harvested after 240 hours to 288 hours or at greater than 50% viability. The experiment was run in at least four separate batches and the average values (II in Table II) for antibody titer, VCC, IVCC and percentage of $G_0F$ and galactosylated glycans are shown in FIG. 1-4.

Alternatively, the experiment as said in Example II was repeated with addition of 8 mM or 12 mM glutamine. The experiment was run in at least four separate batches and the average values (III and IV in Table II) for antibody titer, VCC, IVCC and percentage of $G_0F$ and galactosylated glycans are shown in FIG. 1-4. The percentage of $G_0F$ glycan and galactosylated glycan values for 4 mM, 8 mM and 12 mM glutamine (II-IV respectively) are depicted in Table II.

TABLE II

| | Glycoform composition | | |
|---|---|---|---|
| Experiment | Conc. of L-glutamine (mM) | % Galactosylation | % $G_0F$ |
| I | 0 | 31.4 ± 1.2 | 60.8 ± 1.8 |
| II | 4 | 22.8 ± 1.7 | 68.9 ± 2.0 |
| III | 8 | 18.9 ± 0.4 | 72.8 ± 0.9 |
| IV | 12 | 17.2 ± 0.6 | 73.4 ± 0.3 |

The invention claimed is:

1. A cell culture process for obtaining an anti-VEGF antibody composition comprising the steps of,
   culturing Chinese Hamster Ovary (CHO) cells at a first temperature and a first pH for a first period of time,
   shifting the temperature and the pH to a second value, where the second temperature value is lower than the first temperature and the second pH value is lower than the first pH, and
   supplementing the said culture with glutamine,
wherein the concentration of glutamine in the culture is about 4 mM to about 12 mM, and
wherein the change in temperature and pH is done simultaneously at about two days to about three days after the inoculation of cell culture, thereby obtaining the antibody composition comprising of about 16% to about 25% galactosylated glycan and/or about 66% to about 74% G0F glycan.

2. The process according to claim 1, wherein glutamine is supplemented to the culture when integral viable cell concentration (IVCC) of the cells in the culture is between about 10 million cells/day/ml to about 20 million cells/day/ml.

3. The process according to claim 1, wherein the difference in the first and the second temperature is about 2° C. to about 7° C.

4. The process according to claim 1, wherein the difference in the first and second pH is about 0.1 to about 0.5 units of pH.

5. The process according to claim 1, wherein said second pH is maintained until harvest of cells.

6. A cell culture process for increasing the $G_0F$ glycans in an anti-VEGF antibody composition, the process comprising the steps of,
   culturing Chinese Hamster Ovary (CHO) cells at first temperature and first pH for a first period of time,
   shifting the temperature and the pH to a second value, where the second value is lower than the first temperature and first pH,
   supplementing the said culture with glutamine,
wherein the concentration of glutamine in the culture is about 4 mM to about 12 mM, and
wherein the change in temperature and pH is done simultaneously at about two days to about three days after the inoculation of cell culture and wherein the increase is of about 13% to about 21% when compared to an antibody composition obtained by a process without addition of glutamine.

7. The process according to claim 6, wherein glutamine is added to the culture when integral viable cell concentration (IVCC) of the cells in the culture is between about 10 million cells/day/ml to about 20 million cells/day/ml.

8. The process according to claim 6, wherein the difference in the first and the second temperature is about 2° C. to about 7° C.

9. The process according to claim 6, wherein the difference in the first and second pH is about 0.1 to about 0.5 units of pH.

10. The process according to claim 6, wherein said second pH is maintained until harvest of cells.

11. A cell culture process for decreasing the galactosylated glycans in an anti-VEGF antibody composition the process comprising the steps of, culturing Chinese Hamster Ovary (CHO) cells at first temperature and first pH for a first period of time, shifting the temperature and the pH to a second value, where the second value is lower than the first temperature and first pH supplementing the said culture with glutamine, wherein the concentration of glutamine in the culture is about 4 mM to about 12 mM, and wherein the change in temperature and pH is done simultaneously at about two days to about three days after the inoculation of cell culture and wherein the decrease is of about 27% to about 46% when compared to an antibody composition obtained by a process without addition of glutamine.

12. The process according to claim 11, wherein glutamine is added to the culture when integral viable cell concentration (IVCC) of the cells in the culture is between about 10 million cells/day/ml to about 20 million cells/day/ml.

13. The process according to claim 11, wherein the difference in the first and the second temperature is about 2° C. to about 7° C.

14. The process according to claim 11, wherein the difference in the first and second pH is about 0.1 to about 0.5 units of pH.

15. The process according to claim 11, wherein said second pH is maintained until harvest of cells.

* * * * *